United States Patent [19]
Gawreluk

[11] Patent Number: 5,800,410
[45] Date of Patent: Sep. 1, 1998

[54] CATHETER WITH STRESS DISTRIBUTION FINGERS

[75] Inventor: Craig N. Gawreluk, Park City, Utah

[73] Assignee: Becton Dickinson and Company, Franklin Lakes, N.J.

[21] Appl. No.: 666,775

[22] Filed: Jun. 19, 1996

Related U.S. Application Data

[63] Continuation-in-part of Ser. No. 635,102, Apr. 19, 1996.
[51] Int. Cl.$^6$ .................................................. A61M 25/00
[52] U.S. Cl. ........................................... 604/280; 604/282
[58] Field of Search ................................. 604/280, 282, 604/283, 284, 905, 264

[56] References Cited

U.S. PATENT DOCUMENTS

| | | | |
|---|---|---|---|
| 4,013,310 | 3/1977 | Dye. | |
| 4,323,065 | 4/1982 | Kling. | |
| 5,330,449 | 7/1994 | Prichard et al. | 604/282 |
| 5,358,493 | 10/1994 | Schweich et al. | 604/264 |
| 5,380,301 | 1/1995 | Prichard et al. | 604/281 |
| 5,466,230 | 11/1995 | Davilla | 604/256 |
| 5,533,985 | 7/1996 | Wang | 604/264 |
| 5,599,325 | 2/1997 | Ju et al. | 604/282 |

FOREIGN PATENT DOCUMENTS

WO 94/01161  1/1994  WIPO.

*Primary Examiner*—Mark Bockelman
*Assistant Examiner*—Jennifer R. Sadula
*Attorney, Agent, or Firm*—Eric M. Lee

[57] ABSTRACT

This invention relates to a catheter having a hub or extension tube connected to the catheter cannula and including at least one stress distribution finger extending from the distal end of the extension tube around the catheter cannula at the junction between the extension tube and the catheter cannula. These stress distribution fingers distribute any stress exerted at the junction between the extension tube and the catheter cannula to avoid stress localization and improve the pull strength of the catheter.

6 Claims, 2 Drawing Sheets

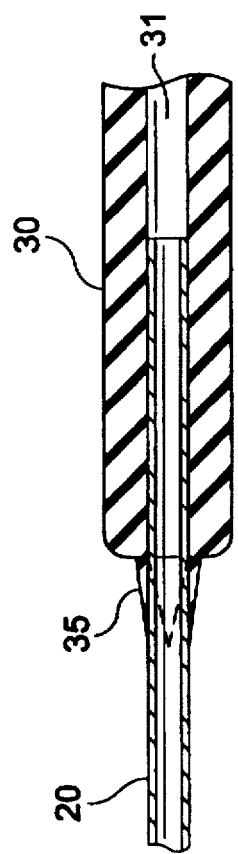
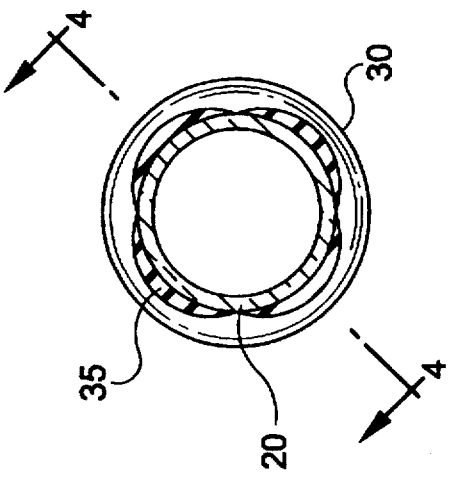
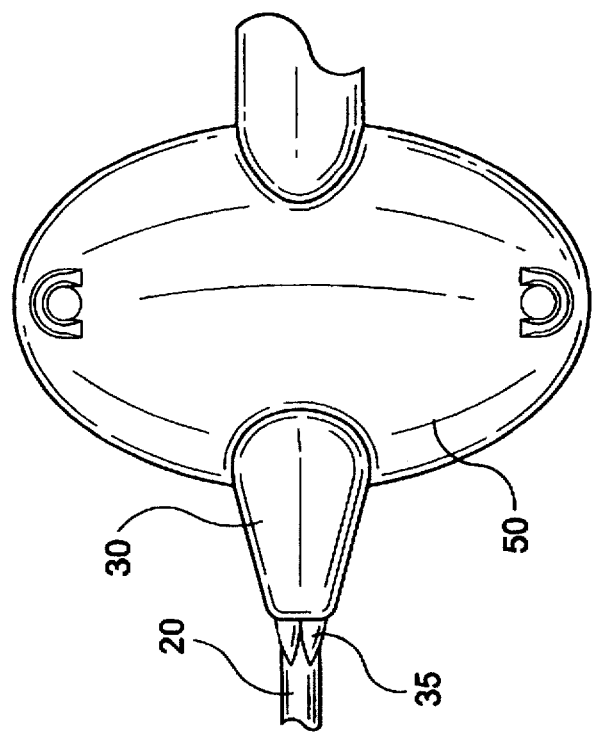

CATHETER WITH STRESS DISTRIBUTION FINGERS

This application is a continuation-in-part application of co-pending application Ser. No. 08/635,102 filed Apr. 19, 1996.

BACKGROUND OF THE INVENTION

This invention relates to the field of intravenous (IV) catheters. This invention has particular applicability, but is not limited, to peripherally inserted central catheters (PICCs) incorporating a silicone cannula.

Typical peripheral IV catheters are used to gain access to a patient's venous system so the patient can be infused with medicaments, IV solutions or other fluids. The proximal end of such a catheter usually includes a hub that is designed to be connected to a fluid supply line or other medical device such as a syringe or a valve or IV pump. The cannula of these types of catheters are on the order of about one to two inches long. The cannula is either polyurethane or Teflon.

These peripheral IV catheters are typically placed in one of the patient's smaller veins located in the hand or arm with the hub taped to the patient's skin. Since peripheral IV catheters are short, taping the catheter to the patient's skin minimizes the possibility that the catheter will become dislodged from the patient's vein if the patient moves or a clinician manipulates the catheter to connect or disconnect an IV line or other medical device. Peripheral IV catheters may also include extension tubes which extend proximally from the proximal end of the catheter that is inserted into the patient and which include a hub at the proximal end. Such extension tubes can be taped to the patient's skin. Because of biocompatibility issues, typical polyurethane or Teflon peripheral IV catheters are generally kept in a patient only up to about 72 hours. After this time a new peripheral IV catheter must be inserted into the patient.

For certain types of IV therapy, it is important for the distal tip of the catheter to be located in the auxiliary, subclavian or brachiocephalic vein or in the superior vena cava. This is necessary because certain medicaments are extremely harsh. Thus, it is important to have the medicament diluted quickly in a large vein to prevent adverse reaction by the patient. Heretofore, centrally inserted venous access catheters have been used for this type of IV therapy because such catheters can be inserted directly into the large veins of a patient. A drawback of these types of catheters is that placement of such catheters into a patient is considered a surgical procedure which requires a physician.

PICCs are an alternative to centrally inserted, tunneled or implanted venous access devices. PICCs are generally longer than standard peripheral IV catheters. They are inserted into a patient's vein in the arm and advanced through the venous system until the tip is located in the auxiliary, subclavian or brachiocephalic vein or in the superior vena cava. Typical PICC tubing is formed from silicone or some other biocompatible, soft, flexible polymer. Because of this PICCs can remain in place in a patient for several weeks, months or years. PICCs are thus used for patients needing IV antibiotic therapy for more than seven days, hyperalimentation, chemotherapy, long term IV rehydration or other long term IV therapy.

Many PICCs are currently available. These products work satisfactorily for their intended purpose but could be improved. For example, most PICCs typically include an extension tube connected to the proximal end of the catheter cannula. The extension tube is typically thicker and substantially stronger than the catheter cannula. This results in an abrupt transition in strength between the extension tube and the catheter cannula. Any force applied to the PICC tending to pull the extension tube away from the catheter cannula will cause localized stress at the junction between the catheter cannula and the extension tube. For catheters such as PICCs that are formed from silicone, this is a significant problem because silicone tubing is sensitive to radial stress. Thus, PICCs are prone to failure at the junction between the catheter cannula and the extension tube.

SUMMARY OF THE INVENTION

It is therefore an object of this invention to provide a mechanism that smoothes the transition between the catheter cannula and the extension tube of a catheter.

It is another object of this invention to provide a mechanism for distributing the stress between the catheter cannula and the extension tube of a catheter.

The catheter of this invention comprises a cannula connected at its proximal end to the distal end of a low profile extension tube. This low profile extension tube includes a lumen in communication with the lumen of the cannula. At least one, and preferably a plurality of stress distribution fingers extend distally from the distal end of the extension tube about the circumference of the proximal portion of the catheter cannula. These stress distribution fingers serve to redistribute the stress applied to the junction between the extension tube and the catheter cannula along the width and length of the stress distribution fingers by smoothing the transition between the extension tube and the catheter cannula.

BRIEF DESCRIPTION OF THE DRAWINGS

The above and other objects of this invention will be apparent from the detailed description and drawings in which like parts are referred to by like numbers throughout, and in which:

FIG. 2 is a top plan view of a portion of the single lumen PICC shown in FIG. 1;

FIG. 3 is an enlarged immediate cross-sectional view taken along line 3—3 of FIG. 1 showing just the cross-section of the catheter cannula and the stress distribution fingers and the distal end of the extension tube; and FIG. 4 is an enlarged cross-sectional view taken along line 4—4 of FIG. 3.

DETAILED DESCRIPTION OF THE INVENTION

Figure 1:
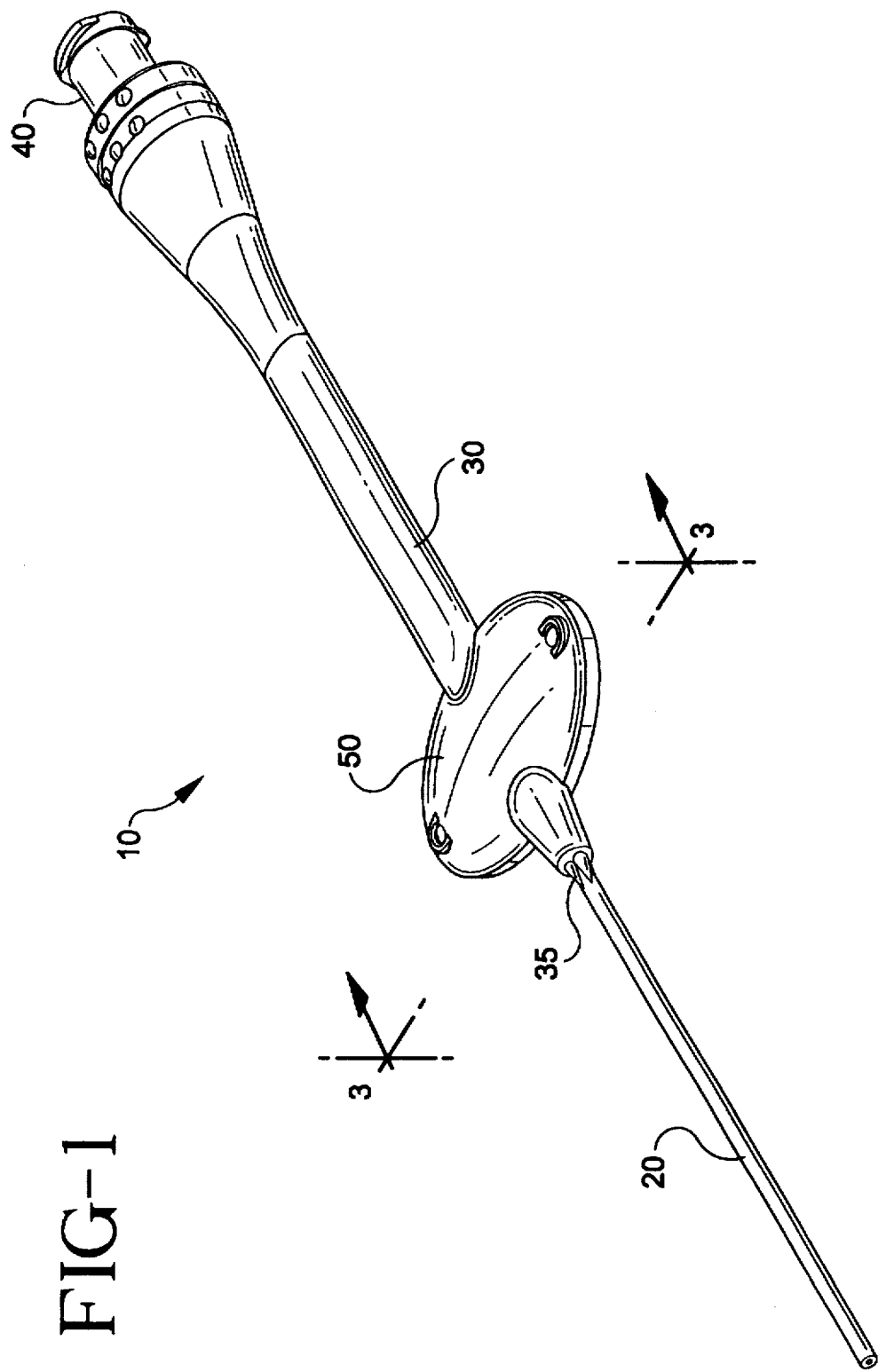
FIG. 1 is a perspective view of a single lumen PICC having a low profile extension tube, wing, and barbed luer adapter and incorporating the stress distribution fingers of this invention.

The catheter assembly 10 of this invention includes a cannula 20, a hub or extension tube 30 and a luer adapter 40 at the proximal end of extension tube 30. A wing 50 may be formed integrally with extension tube 30.

Cannula 20 has a single lumen extending therethrough. However, cannula 20 may include two lumens extending therethrough. Where cannula 20 includes two lumens, catheter assembly 10 includes two extension tubes. Preferably cannula 20 is formed from a soft, biocompatible material such as silicone. Cannula 20 is preferably formed by extruding the silicone with the desired dimensions and configuration.

Extension tube 30 includes a central lumen 31 extending therethrough and is formed from a soft, flexible material such as silicone rubber having a durometer of between about 65 Shore A to about 45 Shore A. Extension tube 30, either with or without wing 50, and central lumen 31 is formed by injection molding extension tube 30 in a die with a core pin placed in the die. Extension tube 30 is overmolded onto cannula 20 which ensures a solid bond therebetween since extension tube 30 and cannula 20 are formed from similar materials.

Extension tube 30 is formed with at least one and preferably a plurality of stress distribution fingers 35 located at its distal end. Any number of stress distribution fingers 35 could be used. However, it has been determined that greater benefits are achieved when more than one stress distribution finger is used. For example, preferably three stress distribution fingers are used on a 2FR catheter, four stress distribution fingers are used on catheters between 2FR and 5FR in size and five or more stress distribution fingers are used on catheters larger than 5FR. These stress distribution fingers preferably are located around cannula 20 in the angular orientation such as shown in FIG. 3. However, it is to be understood that other angular orientations could also be used. These stress distribution fingers 35 are formed when extension tube 30 is overmolded onto cannula 20 by creating the mold for extension tube 30 with these stress distribution fingers.

Each stress distribution finger 35 should extend at least about 0.060 inches, and preferably at least about 0.080 inches, beyond the distal end of extension tube 30. In addition, each stress distribution finger 35 has a thickness that decreases in the distal direction. Preferably each stress distribution finger 35 has a maximum thickness of about 200% of the wall thickness of cannula 20. The combination of the maximum thickness and length of each stress distribution finger 35 results in a taper angle of between about 20° to about 10°. This angle ensures that each stress distribution finger 35 smoothly transitions from the distal end of extension tube 30 to cannula 20.

The following two experiments were conducted to quantify the improvement in catheters incorporating stress distribution fingers.

In the first experiment, three sets of catheters were tested. One set did not include any stress distribution fingers. One set incorporated only one stress distribution finger. One set incorporated four stress distribution fingers. All of the catheters were comprised of a silicone cannula and a silicone rubber extension tube. In addition, all of the catheters were four FR (French) in size and were six inches long. All catheters were pull tested on a standard Instron 50 pound load cell where the extension tube was clamped and the catheter cannula was clamped. The load at breakage was recorded with the results set forth below.

| No. of Stress Distribution Fingers | Average Pull Strength (lbs.) | Standard Deviation |
| --- | --- | --- |
| 0 | 1.214 | 0.099 |
| 1 | 1.642 | 0.23 |
| 4 | 1.910 | 0.281 |

As is apparent from the above data, the catheters incorporating four stress distribution fingers had an average pull strength of 0.268 pounds higher than catheters with only one stress distribution finger. This is a 14% improvement in pull strength. In addition, the catheters incorporating four stress distribution fingers had an average pull strength of 0.696 pounds higher than catheters without any stress distribution fingers. This is a 36.4% improvement in pull strength.

In the second experiment, two sets of catheters were tested. One set did not include any stress distribution fingers while the other set incorporated four stress distribution fingers. All of the catheters were comprised of a silicone cannula and a silicone rubber extension tube. In addition, all of the catheters were three FR (French) in size and were four inches long. All catheters were pull tested on a standard Instron 50 pound load cell where the extension tube was clamped and the catheter cannula was clamped. The load at breakage was recorded with the results set forth below.

| No. of Stress Distribution Fingers | Average Pull Strength (lbs.) | Standard Deviation |
| --- | --- | --- |
| 0 | 0.782 | 0.051 |
| 4 | 1.069 | 0.074 |

As is apparent from the above data, the catheters incorporating four stress distribution fingers had an average pull strength of 0.287 pounds higher than catheters without any stress distribution fingers. This is a 26.8% improvement in pull strength.

Thus, it is seen that a catheter is provided that has a mechanism for smoothing the transition between the catheter cannula and the extension tube so as to distribute the stress at that transition.

I claim:

1. A medical device, comprising:

an elongate cannula formed from a soft and flexible material and having a wall thickness;

an abutting element formed from the soft and flexible material and having a distal end operatively connected to the elongate cannula and forming a junction therebetween; and a plurality of stress distribution fingers formed from the soft and flexible material and extending from the distal end of the abutting element at the junction over the cannula wherein each stress distribution finger has a proximal end with a first width abutting the distal end of the abutting element and a distal end having a second width that is less than the first width and sides that taper from the proximal end to the distal end so as to define an undulating interface between the sides and second width of each stress distribution finger and the cannula.

2. The medical device of claim 1 wherein the soft and flexible material is silicone.

3. The medical device of claim 2 wherein each stress distribution finger has a thickness that decreases from the proximal end toward the distal end.

4. The medical device of claim 3 wherein the thickness of each stress distribution finger decreases at an angle of between about 2° and about 10°.

5. The medical device of claim 4 wherein each stress distribution finger has a maximum thickness of about 200% of the wall thickness of the cannula.

6. The medical device of claim 2 wherein each stress distribution finger has a length of at least about 0.060 inches.

* * * * *